United States Patent [19]

D'Silva

[11] 4,091,016

[45] May 23, 1978

[54] THIOSULFENYLCARBAMOYL HALIDES

[75] Inventor: Themistocles D. J. D'Silva, South Charleston, W. Va.

[73] Assignee: Union Carbide Corporation, New York, N.Y.

[21] Appl. No.: 618,889

[22] Filed: Oct. 2, 1975

Related U.S. Application Data

[63] Continuation-in-part of Ser. No. 486,631, Jul. 8, 1974.

[51] Int. Cl.$^2$ .................. C07C 125/00; C07C 125/03
[52] U.S. Cl. .......................... 260/544 C; 260/465 D; 260/465.4
[58] Field of Search ............... 260/544 C, 464, 465 D, 260/465.4

[56] References Cited

U.S. PATENT DOCUMENTS

| | | | |
|---|---|---|---|
| 3,282,950 | 11/1966 | Ottoman et al. | 260/544 C |
| 3,879,190 | 4/1975 | Fuchs | 260/544 C |

*Primary Examiner*—Norman Morgenstern
*Attorney, Agent, or Firm*—Robert C. Brown

[57] ABSTRACT

N-Thiosulfenylcarbamoyl halide compositions are useful intermediates in the production of carbamate compositions.

11 Claims, No Drawings

THIOSULFENYLCARBAMOYL HALIDES

This application is a continuation-in-part of my copending U.S. patent application Ser. No. 486,631 filed July 8, 1974.

This invention relates to novel carbamoyl halide compositions and to their preparation.

The novel compositions of this invention are compounds corresponding to the following general formula:

$$X-\underset{\underset{O}{\|}}{C}-\underset{\underset{R}{|}}{N}-S-S-R_1$$

wherein;

X may be fluorine or chlorine

R may be lower alkyl, lower alkenyl or lower alkyl substituted with one or more chloro, bromo, fluoro, nitro or cyano substituents or phenyl or lower phenyl alkyl either unsubstituted or substituted with one or more chloro, bromo, fluoro, nitro, cyano, lower alkyl, lower haloalkyl or lower alkoxy substituents.

$R_1$ may be alkyl, alkenyl, cycloalkyl, bicycloalkyl, cycloalkenyl or bicycloalkenyl or lower phenylalkyl or phenyl or lower phenylalkyl or phenyl substituted with one or more chloro, bromo, fluoro, nitro, cyano, lower alkyl, lower alkoxy, lower haloalkyl, lower alkanoyl or carbamoyl substituents.

These compounds are valuable intermediates which are useful in the preparation of insecticidal compositions. Compositions of this invention can be reacted with oxime compositions such as 1-methylthioacetaldoxime, in an aprotic solvent and in the presence of an acid acceptor such as triethylamine as more fully described in my copending U.S. patent application Ser. No. 486,632 filed July 8, 1974, to produce insecticidal and miticidal compositions.

The novel compositions of this invention can be prepared in a variety of ways. One preferred method of preparation is by the process shown in the following general reaction scheme:

$$F-\underset{\underset{O}{\|}}{C}-\underset{\underset{R}{|}}{N}-H + X-S-S-R_1 \longrightarrow F-\underset{\underset{O}{\|}}{C}-N\diagup^{R}_{\diagdown S-S-R_1} \quad \text{I}$$

They may also be prepared by the following process:

$$X-C\underset{\underset{O}{\|}}{N}\diagup^{R}_{\diagdown SCl} + HSR_1 \longrightarrow X-C\underset{\underset{O}{\|}}{N}\diagup^{R}_{\diagdown S-S-R_1} \quad \text{II}$$

A third method of producing these compositions is as follows:

$$R-NH_2 + X-S-S-R_1 \longrightarrow HN\diagup^{R}_{\diagdown S-S-R_1} \quad \text{III}$$

$$HN\diagup^{R}_{\diagdown S-S-R_1} + COX_2 \longrightarrow X-\underset{\underset{O}{\|}}{C}-N\diagup^{R}_{\diagdown S-S-R_1}$$

In each of the three general reaction schemes shown above X, R and $R_1$ are as defined above.

These reactions are preferably carried out in an aprotic solvent such as toluene, benzene, xylene, dioxane methylene chloride or the like.

These reactions are carried out in the presence of an organic base, preferably a tertiary amine such as triethyl amine.

Illustrative of the new compositions of matter which can be prepared by the above processes are the following:

N-Methyl-N-(methylthiosulfenyl)carbamoyl fluoride
N-Ethyl-N(methylthiosulfenyl)carbamoyl fluoride
N-Butyl-N(methylthiosulfenyl)carbamoyl fluoride
N-Allyl-N(methylthiosulfenyl)carbamoyl fluoride
N-Phenyl-N(methylthiosulfenyl)carbamoyl fluoride
N-Methyl-N(methylthiosulfenyl)carbamoyl chloride
N-Methyl-N(ethylthiosulfenyl)carbamoyl chloride
N-Methyl-N(propylthiosulfenyl)carbamoyl chloride
N-Methyl-N(isopropylthiosulfenyl)carbamoyl fluoride
N-Methyl-N-2(2-methylpropanethiosulfenyl)carbamoyl fluoride
N-Methyl-N(n-octylthiosulfenyl)carbamoyl fluoride
N-Methyl-N(dodecylthiosulfenyl)carbamoyl fluoride
N-Methyl-N-(octadecylthiosulfenyl)carbamoyl fluoride
N-Methyl-N-(t-octylthiosulfenyl)carbamoyl fluoride
N-Phenyl-N-2(2-methylpropanethiosulfenyl)carbamoyl chloride
N-Allyl-N-(butylthiosulfenyl)carbamoyl chloride
N-p-chlorophenyl-N(methylthiosulfenyl)carbamoyl fluoride
N-(2-Chloroethyl)-N(methylthiosulfenyl)carbamoyl fluoride
N-(2-Nitroethyl)-N(methylthiosulfenyl)carbamoyl fluoride
N-(3-Cyanopropyl)-N(methylthiosulfenyl)carbamoyl fluoride
N-Benzyl-N(methylthiosulfenyl)carbamoyl fluoride
N-(4-Chlorobenzyl)-N(methylthiosulfenyl)carbamoyl fluoride
N-(3-Nitrophenyl)-N(methylthiosulfenyl)carbamoyl fluoride
N-(4-Methylphenyl)-N(methylthiosulfenyl)carbamoyl fluoride
N-(4-Methoxyphenyl)-N(methylthiosulfenyl)carbamoyl fluoride
N-(4-Trifluoromethylphenyl)-N(methylthiosulfenyl)carbamoyl fluoride
N-(4-Cyanophenyl)-N(methylthiosulfenyl)carbamoyl fluoride
N-Methyl-N(allylthiosulfenyl)carbamoyl fluoride
N-Methyl-N(cyclopentylthiosulfenyl)carbamoyl fluoride
N-Methyl-N(bicyclodecylthiosulfenyl)carbamoyl fluoride
N-Methyl-N(benzylthiosulfenyl)carbamoyl fluoride
N-Methyl-N(4-bromobenzylthiosulfenyl)carbamoyl fluoride N-Methyl-N(3-nitrophenylthiosulfenyl)carbamoyl fluoride N-Methyl-N(4-cyanophenylthiosulfenyl)carbamoyl fluoride N-Methyl-N(4-t-butylphenylthiosulfenyl)carbamoyl fluoride N-Methyl-N(4-methoxyphenylthiosulfenyl)carbamoyl fluoride N-Methyl-N(4-trifluoromethylphenylthiosulfenyl)-carbamoyl fluoride N-Methyl-N(2,4-dichlorophenylthiosulfenyl)carbamoyl fluoride N-Methyl-N(4-methylphenylthiosulfenyl)carbamoyl fluoride N-Methyl-N(4-dimethylcarbamoylphenylthiosulfenyl)carbamoyl fluoride N-Methyl-N(4-acetylphenylthiosulfenyl)carbamoyl fluoride The following examples are provided to more clearly illustrate the procedures for producing the novel compositions of this invention.

EXAMPLE I

Preparation of N-Methyl-N(methylthiosulfenyl)carbamoyl Fluoride (Method I)

To a solution of 7.59 g hydrogenfluoride in 50 ml toluene, cooled to −50° C, was added dropwise with stirring 21.62 g methylisocyanate. After stirring for 1 hour 55.0 g methylthiosulfenyl chloride in 200 ml toluene was added followed by dropwise addition of 38.3 g of triethylamine. The reaction temperature during the addition of base was maintained between 0° and 10° C. Stirring continued for additional 1 hour after the addition of base was completed. The precipitated salt was filtered off and the filtrate concentrated under vacuo. Distillation yielded 16.7 g of pure product b.p. 42° C/0.2 Torr, $N_D^{24}$ 1.5096.

Calc'd. for $C_3H_6FNOS_2$: C, 23.22, H, 3.89, N, 9.02. Found: C, 23.39, H, 4.18, N, 8.75.

IR (Neat) 5.58 (C=O), 7.05, 7.7, 8.4, 8.6, 9.2, 9.35, 10.6, 13.4 and 14.35 μ.

NMR (CDCl$_3$), δ 2.69, (singlet), 3H, CH$_3$S, 3.28, (doublet), J = 1.0 H$_z$,3H, CH$_3$N.

EXAMPLE II

Preparation of N-Methyl-N(2-Methyl-2-Propanethiosulfenyl) Carbamoyl Fluoride (Method I)

To a solution of 231.08 N-methylcarbamoyl fluoride, (prepared in situ as before) in 600 ml toluene, cooled to 0° C was added 478.0 g 2-methyl-2-propanethiosulfenyl chloride dissolved in 1000 ml toluene. This was followed by dropwise addition of 303.0 g triethylamine in 1000 ml of toluene. Stirring was continued for an additional 2 hr. at 5° C. The precipitated salt was filtered off the filtrate concentrated. Wt. of reddish oil 577.0 g b.p. 75°–80° C/0.5 Torr. $N_D^{22}$ 1.4983.

IR(Neat 5.6 (C=O), 6.9, 7.7, 8.65, 9.25, 9.4 (sh), 10.62 and 13.4 μ

NMR(CDCl$_3$) δ 1.4, (S), 9H, t-Bu; 3.23 (d), J=1.0 H$_z$, 3H, CH$_3$N.

EXAMPLE III

Preparation of N-Methyl-N-(n-Octylthiosulfenyl)Carbamoyl Fluoride (Method I)

Prepared as above by adding 25.2 g triethylamine to a solution of 48.0 g. n-octylthiosulfenylchloride and 19.26 g N-methylcarbamoyl fluoride. b.p. 110°–118° C/0.2 Torr. $N_D^{21}$ 1.4900.

IR(Neat) 5.58 (C=O) ,6.9–7.1 (broad), 7.7, 8.4, 8.6, 9.2–9.35 (broad), 10.4 (Sh), 10.58, 13.4, 13.9 and 14.3 μ.

NMR(CDCl$_3$), δ 0.88, (t), J∼5.0 H$_z$, 3H, CH$_3$; 1.1–1.9 (m), 12H, CH$_2$, 2.99, (t), J=7.0 H$_z$, 3H, —CH$_2$S—; 3.25, d, $J_{HF}$∼1.0 H$_z$, 3H, CH$_3$ N.

Calc'd. for $C_{10}H_{20}FNOS_2$: C, 47.40; H, 7.96; N, 5.53. Found: C, 47.22, H, 7.27, N, 5.43.

EXAMPLE IV

Preparation of N-Methyl-N(4-t-Butylphenylthiosulfenyl) Carbamoyl Fluoride (Method I)

To a solution of 5.5 g hydrogen fluoride in toluene cooled to −65° C was added dropwise with stirring 15.0 ml of methylisocyanate over a period of 20 minutes after stirring for 1.5 hr preshly prepared 4-t-butylphenylthiosulfenyl chloride (prepared from 36.2 g 4-t-butylthiophenol and 31.0 g sulfur dichloride in 800 ml ethyl ether) was added at −10° to 0° C over a period of 0.5 hr. After stirring overnight at ambient temperature, the salt was removed by filtration and the filtrate distilled. b.p. 122°–127° C/0.2 Torr.

IR(Neat) 5.6 (C=O) and other import peaks at 7—7, 9.3, 10.55, 12—12 and 13.4μ

NMR(CDCl$_3$) δ 1.27, (S), 9H; 3.15, (d) δ–1.0 H$_z$, 3H, 7.3–7.6 (m), 4H.

EXAMPLE V

Preparation of N-Methyl-N(2,4-Dichlorophenylthiosulfenyl)Carbamoyl Fluoride (Method II)

An essentially equimolar amount of N-methyl-N-chlorosulfenylcarbamoylfluoride in toluene solvent is added to 2,4-dichlorophenylthiol after the evolution of hydrochloric acid gas is ceased the solvent is removed under reduced pressure to yield the product.

EXAMPLE VI

Preparation of N-Allyl-N(Butylthiosulfenyl)Carbamoyl Chloride (Method III)

An essentially equimolar amount of allyl amine and an equimolar amount of triethylamine is added slowly with stirring to a quantity of butyldithiochloride in toluene until the reaction is complete. The resulting salt precipitate is removed by filtration. An equimolar amount of triethylamine base is then added to the filtrate followed by the slow addition of phosgene until the reaction is complete. The resulting N-Allyl-N-(butylthiosulfenyl)carbamoyl chloride product is separated and purified by the procedure described above.

EXAMPLE VII

Preparation of N-Methyl-N(i-Propylthiosulfenyl)Carbamoyl Fluoride (Method I)

Prepared by the procedure of Example II by reacting isopropylthiosulfenyl chloride with methylcarbamoyl fluoride. b.p. 43°–45° C/0.5 Torr. $N_D^{21} = 1.4986$.

IR(Neat) 5.56μ(C=O) NMR(CDCl$_3$) δ1.37(d) J=7.0 H$_2$ (iPr), 3.24(d) J∼1.5 H$_2$ NCH$_3$.

Calc'd for $C_5H_{10}FNOS_2$: C, 32.77; H, 5.50; N, 7.64. Found: C, 33.73; H, 5.53; N, 6.68.

EXAMPLE VIII

Preparation of N-Methyl-N-(n-Butylthiosulfenyl)Carbamoyl Fluoride (Method I)

Prepared by the procedure of Example II by reacting n-butylthiosulfenyl chloride with methylcarbamoyl fluoride b.p. 68°–70° C/0.15 Torr Calc'd for $C_6H_{12}FNOS_2$: C, 36.38; H, 6.51; N, 7.07. Found: C, 37.76; H, 6.30; N, 6.67.

EXAMPLE IX

Preparation of N-Methyl-N(t-Octylthiosulfenyl)Carbamoyl Fluoride (Method I)

Prepared by the procedure of Example II by reacting t-octylthiosulfenylchloride with methylcarbamoyl fluoride. b.p. 112° C/0.5 Torr $N_D^{23}$ 1.4960.

Calc'd for $C_{10}H_{20}FNOS_2$: C, 47.42; H, 7.96; N, 5.53. Found: C, 47.42; H, 7.90; N, 5.34.

EXAMPLE X

Preparation of N-Methyl-N(Cyclohexylthiosulfenyl)Carbamoyl Fluoride (Method I)

Prepared by the procedure of Example II by reacting cyclohexanethiosulfenyl chloride with methylcarbamoyl fluoride. $N_D^{23}$ 1.5335.

Calc'd for $C_8H_{14}FNOS_2$: C, 43.02; H, 6.31; N, 6.26. Found: C, 43.97; H, 6.58; N, 4–86.

EXAMPLE XI

Preparation of N-Methyl-N(Phenylthiosulfenyl)Carbamoyl Fluoride (Method I)

Prepared by the procedure of Example II by reacting phenylthiosulfenyl chloride with methylcarbamoyl fluoride. b.p. 100°–110° C/0.3 Torr $N_D^{22.5}$ 1.5770.

NMR (CDCl$_3$) δ3.09 (d) J∼1.0, NCH$_3$; 7.1–7.7 m Aromatic.

Calc'd for $C_8H_8FNOS_2$: C, 44.22; H, 3.71; N, 6.44. Found: C, 45.61; H, 3.95; N, 5–90.

EXAMPLE XII

Preparation of N-Methyl-N(4-Methylphenylthiosulfenyl)Carbamoyl Fluoride (Method I)

Prepared by the procedure of Example II by reacting 4-methylphenylthiosulfenyl chloride with methylcarbamoyl fluoride. b.p. 92°–100° C/0.25 Torr $N_D^{22.5}$ 1.5735.

NMR(CDCl$_3$) δ2.30 (s) CH$_3$; 3.14 (d) J∼1.5 NCH$_3$ 7.0 – 7.6 (m) Aromatic (4H).

Calc'd for $C_9H_{10}FNOS_2$: C, 46.73; H, 4.36; N, 6.05. Found; C, 46.82; H, 4.54; N, 6.08.

EXAMPLE XIII

Preparation of N-Methyl-N(4-Chlorophenylthiosulfenyl)Carbamoyl Fluoride (Method I)

Prepared by the procedure of Example II by reacting 4-chlorophenylthiosulfenyl chloride with methylcarbamoyl fluoride. b.p. 110°–113° C/0.3 Torr $N_D^{24}$ 1.5959.

NMR (CDCl$_3$) δ3.18 (d) J∼1.0 NCH$_3$; 7.2–7.7 (m) (4H) Aromatic.

Cald'd for $C_8H_7ClFNOS_2$: C, 38.17; H, 2.80; N, 5.56. Found: C, 38.53; H, 2.99; N, 5–69.

EXAMPLE XIV

Preparation of N-Methyl-N(Phenylthiosulfenyl)Carbamoyl Fluoride (Method II)

To a solution of 0.5 g of thiophenol in 25 ml of pentane was added 0.64 g of N-Methyl-N-chlorothiocarbamoyl fluoride. The immediate exotherm caused the evolution of hydrochloric acid gas. The product obtained on cocentration was identical (by infrared and n.m.r.) to that obtained by Method I.

EXAMPLE XV

Preparation of N-Methyl-N(4-t-Butylphenylthiosulfenyl) Carbamoyl Fluoride (Method II)

Prepared by reacting 0.5 g of 4-t-butylthiophenol in pentane with 0.44 g of N-methyl-N-chlorothiocarbamoyl fluoride. The reaction proceded with a vigorous exotherm and evolution of hydrochloric acid gas. The infrared and n.m.r. spectra of the product was identical to the material prepared by Method I.

EXAMPLE XVI

Preparation of N-Methyl-N(4-t-Butylphenylthiosulfenyl) Carbamoyl Chloride (Method II)

To a solution of 20.79 g of 4-t-butylthiophenol in 150 ml of pentane was added dropwise with stirring 20 g of N-methyl-N-chlorothiocarbamoyl chloride. After the addition was completed the reaction mixture was heated under reflux for 1 hour. On concentration under reduced pressure it yielded the product as an oil.

IR(Neat) 5.78 (C=O), NMR (CDCl$_3$) δ1.3 (S), (9H); 3.27 (S), NCH$_3$.

Calc'd for $C_{12}H_{16}ClNOS_2$: C, 49.72; H, 5.56; N, 4.83. Found: C, 50.04; H, 5.36; N, 4.50.

These compounds are valuable intermediates for the preparation of insecticidal compositions. Compounds of this invention can be reacted with oxime compounds in accordance with the following general reaction scheme:

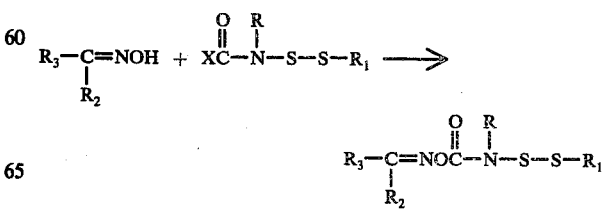

where

R, $R_1$ and X are as described above and, $R_2$ may be lower alkyl or lower alkyl substituted with one or more chloro, bromo, fluoro, nitro or cyano substituents or phenyl or lower phenyl alkyl either unsubstituted or substituted with one or more chloro, bromo, fluoro, nitro, cyano, lower alkyl or lower alkoxy substitutents.

$R_3$ may be alkyl, alkenyl, cycloalkyl, bicycloalkyl, cycloalkenyl, bicycloalkenyl or phenyl or lower phenyl alkyl either unsubstituted or substituted with one or more chloro, bromo, fluoro, nitro, cyano, lower alkyl, lower alkoxy or lower haloalkyl substituents.

The reaction set forth above is preferably carried out in an aprotic solvent such as dioxane, toluene, xylene or benzene and in the presence of a base such as a tertiary amine or an alkaline earth base.

The following example is a more specific illustration of the use of the compounds of this invention in the preparation of pesticidally active compounds.

EXAMPLE VII

1-Methylthioacetaldehyde O-([N-methyl-N-(2-methyl-2-propanethiosulfenyl)carbamoyl]oxime To a solution of 2.83 g (0.027 m) of 1-methylthioacetaldoxime and 11.15 g (0.027 m) of N-methyl-N-(2-methyl-2-propanethiosulfenyl)carbamoyl fluoride in 75 ml of dioxane, was added dropwise 2.72 g (0.027 m) of triethylamine. After stirring for 72 hours at ambient temperature the reaction mixture was concentrated under reduced pressure, it was diluted with water and extracted with ethyl acetate. The organic extract was washed with water, dried over magnesium sulfate and concentrated. Crystallized from isopropyl ether-hexane solution to afford a white solid —m.p. 67°-69° C. On recrystallization, m.p. 71°-73° C.

Calc'd for $C_9H_{18}N_2O_2S_3$: C, 38.46; H, 6.40; N, 9.88 Found: C, 38.57; H, 6.20; N, 9.95.

The compound of Example VII was evaluated to determine its pesticidal activity against two-spotted mite (*Tetranychus urticae* Koch) bean aphid (*Aphis fabae* Scop.); Southern Armyworm (*Prodenia eridania*, (Cram)); Mexican beam beetle (*Epilachna varivestic*, Muls.); and housefly (*Musca domestica*, L.). A suspension of the compound was prepared by dissolving one gram of the compound in 50 milliliters of acetone which contained 0.1 gram of an alkylphenoxy polyethoxyethylene surfactant. The resulting solution was successively diluted with water to provide a suspension containing 500 parts of the compound per million parts of final formulation.

The test insect and mite species were sprayed with 100 and 110 milliliters of the test ompound formulation for approximately 25 seconds. The test species were then held for from one to three days at constant temperature and/or constant humidity after which the extent of mortality was recorded. The compound was found to exhibit excellent control of all of the test species.

What is claimed is:

1. Compounds of the formula:

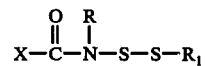

wherein:
X may be fluorine or chlorine.
R may be lower alkyl, lower alkenyl or lower alkyl substituted with one or more chloro, bromo, fluoro, nitro or cyano substituents or phenyl or lower phenyl alkyl either unsubstituted or substituted with one or more chloro, bromo, fluoro, nitro, cyano, lower alkyl, lower haloalkyl or lower alkoxy substituents.
$R_1$ may be alkyl, alkenyl, cycloalkyl, bicycloalkyl, cycloalkenyl or bicycloalkenyl or lower phenylalkyl or phenyl; or lower phenylalkyl or phenyl substituted with one or more chloro, bromo, fluoro, nitro, cyano, lower alkyl, lower alkoxy, lower haloalkyl, lower alkanoyl or carbamoyl substituents.

2. Compounds according to claim 1 where X is fluorine.

3. Compounds according to claim 1 where X is chlorine.

4. Compounds according to claim 1 where R is lower alkyl.

5. Compounds according to claim 1 where $R_1$ is alkyl.

6. Compounds according to claim 1 where $R_1$ is phenyl.

7. Compounds according to claim 1 where $R_1$ is substituted phenyl.

8. Compounds according to claim 1 where R is lower alkyl and $R_1$ is alkyl.

9. N-Methyl-N(methylthiosulfenyl)carbamoyl fluoride.

10. N-Methyl-N(2-methyl-2-propanethiosulfenyl)carbamoyl fluoride.

11. N-Methyl-N-(n-octylthiosulfenyl)carbamoyl fluoride.